United States Patent
Thiessen et al.

(10) Patent No.: US 10,550,444 B2
(45) Date of Patent: Feb. 4, 2020

(54) MOLDED LOOSE GRAIN INSPECTION TOOLS AND METHOD

(71) Applicant: Lear Corporation, Southfield, MI (US)

(72) Inventors: Suzette Thiessen, Auburn Hills, MI (US); Kipp Pascoe, Auburn Hills, MI (US)

(73) Assignee: LEAR CORPORATION, Southfield, MI (US)

( * ) Notice: Subject to any disclaimer, the term of this patent is extended or adjusted under 35 U.S.C. 154(b) by 138 days.

(21) Appl. No.: 15/810,593

(22) Filed: Nov. 13, 2017

(65) Prior Publication Data

US 2019/0144956 A1    May 16, 2019

(51) Int. Cl.

| | |
|---|---|
| *B29C 33/44* | (2006.01) |
| *C14B 1/56* | (2006.01) |
| *C14B 5/02* | (2006.01) |
| *G01N 1/28* | (2006.01) |
| *B29C 33/38* | (2006.01) |
| *C14B 7/02* | (2006.01) |

(52) U.S. Cl.
CPC ............ *C14B 1/56* (2013.01); *B29C 33/3878* (2013.01); *B29C 33/44* (2013.01); *C14B 5/02* (2013.01); *C14B 7/02* (2013.01); *G01N 1/2806* (2013.01); *C14B 2700/18* (2013.01)

(58) Field of Classification Search
CPC ............ B39C 33/3878; B39C 33/3892; B39C 33/3857; B29C 2033/3871

USPC ......................................... 264/220, 225, 222
See application file for complete search history.

(56) References Cited

U.S. PATENT DOCUMENTS

| | | | |
|---|---|---|---|
| 3,298,851 A | | 1/1967 | Fuchs |
| 3,989,790 A | * | 11/1976 | Bruner ................ B29C 33/3857 264/225 |
| 4,294,650 A | | 10/1981 | Werthmann |
| 5,750,160 A | | 5/1998 | Weber et al. |
| 2003/0090030 A1 | * | 5/2003 | Ferguson ............ B29C 33/3857 264/220 |

FOREIGN PATENT DOCUMENTS

| | | |
|---|---|---|
| CN | 202808822 U | 3/2013 |
| DE | 19851117 A1 | 5/2000 |
| DE | 10119494 A1 | 10/2002 |

* cited by examiner

*Primary Examiner* — Christina A Johnson
*Assistant Examiner* — Xue H Liu
(74) *Attorney, Agent, or Firm* — Brooks Kushman P.C.

(57) ABSTRACT

A method for molding or replicating leather samples for inspection, selecting and later using those samples in applications such as automobile interiors with leather surfaces that are laminated or have a loose grain appearance. In one process variant, the main steps include choosing original samples for replication, the original samples including a characteristic to be replicated; making a replication tool from the approved samples; and producing replicated molded samples with the replication tool that emulate the original samples, thereby enabling the replicated molded samples to be compared with the original sample.

8 Claims, 4 Drawing Sheets

Smooth Leather Overview

Smooth Leather Original Sample Selection

Smooth Leather Mold/Tool from Original Sample

Smooth Leather Finished Product - Replicated Leather

Embossed Leather Overview

Embossed Leather
Original Sample Selection

Embossed Leather
Mold/Tool from Original Sample

Embossed Leather Finished
Product - Replicated Leather

MOLDED LOOSE GRAIN INSPECTION TOOLS AND METHOD

BACKGROUND OF THE INVENTION (1) Field of the Invention

One aspect of this disclosure relates to tooling and methods for molding or replicating leather samples for inspection, selecting and later using those samples in applications such as automobile interiors with leather surfaces that are laminated or have a loose grain appearance.

(2) Description of Related Art

In the leather business, a leather supplier is often asked to replicate natural markings that occur on leather hides. Such markings may be for example a scar, a scratch, an insect bite, or a loose break, which is a condition that leather hides show to accommodate growth in the bovine animal. These natural markings are common in the leather business and are hallmarks of leather authenticity.

Not incorporating natural marks into products that use leather is cost-prohibitive. Because of the need to use natural markings, every automotive original equipment manufacturer has a different allowance for what scars or natural markings can be visible in a seat for example or in another automotive component. With leather seats, only natural markings (that occurred during the lifetime of the animal) are allowed. These markings differ from defects or artifacts created in a manufacturing process.

In the past, leather suppliers would have to replicate a scar to guide what is, and is not allowable as defined by each OEM by: (1) looking for a perfect scar; (2) getting the OEM to approve it, and then (3) trying to find reasonable copies of that scar in nature from potentially hundreds of hides and samples that were to be cut repeatedly.

With the diversification of the supply chains, particularly since the recession of 2007, the need for more and more copies of these replicates has grown exponentially. In the past, the supplier would have had to make about 3 sample inspection books; however, now a supplier might be required to provide 35-100 books of each acceptable natural mark and natural marking category for a global automotive program. So, the process of having to replicate samples and/or find that exact scar from a hide in mass production is increasingly difficult and is in fact often infeasible or may produce variable results.

The former process for creating replicates versus finding a live scar from hides cut in mass production of one scar often proceeds as follows: if the leather supplier had a scar that the OEM specified that it wanted as many copies of it as possible, traditional practices involved making a "laminated split" or "laminated top grain". To do this, the conventional process was to make a silicone copy (mold) of that scar, spray the silicone mold with a thin layer of finish and then, with an adhesive, adhere the finish to a piece of split leather.

One problem with such practices is that replication of the actual defect at the onset of production is not one-to-one. A replicate of a scar could be far less severe or an area of hide damage known as "mange" could be more severe than what the OEM originally approved.

Another problem with conventional approaches is that the silicone wears out over time. Therefore, a scar that may be emulated perfectly at the beginning of the replication cycle may become less aggressive over time, depending on the required number of replicates. Mold wear is not reliably predictable. Recreation of a mold using the original leather sample is inaccurate as the silicone flattens the leather. This translates into an adverse fiscal impact for leather suppliers. For example, six inches of leather lost over a hide can translate into $6-10 million dollars very quickly. The impact of not being able to use the original severity of the natural marking could be extremely high.

In some circumstances, PVC or vinyl can replicate leather purses, for example. One way to do this is to replicate an original design such an embroidered flower and create a hard tool nickel mold. A mold maker such as Weber Mfg. (see, e.g., www.webermfg.ca, incorporated by reference) for example uses nickel plates to mold an item such as a fiberglass door, instrument panels or virtually any product that could be replicated with a molded substrate. Thus, the mold maker creates hard tooled molds to replicate a component or part of pattern. For example, a customer may want to create fiberglass doors that look like real wood. The mold maker then makes a mold that the fiberglass company could use to make these doors. Another example is the preparation of a nickel mold of a leather wrapped instrument panel. An instrument panel supplier may use a nickel mold to make plastic replicates of the original leather panels.

The automotive industry uses several types and amounts of leather. It has been reported that about 30 percent of cars sold in North America have leather interiors. http://www.nytimes.com/2003/05/30/travel/driving-rolls-royce-or-hyundai-leather-makes-the-car.html. In the mass production of vehicles with leather surfaces there is a need for molded samples that accurately reflect the appearance and texture of the product.

One way to classify a leather surface is to characterize it as a Level 1-5 surface. The higher the number, the higher is the graininess or looseness.

Leather is also characterized in terms of its a. Quality—grain (natural patterns and blemishes on the hide; full-grain is the most natural and least processed; top grain is from the hide's outer layer and is often sanded);

b. Type—for example, nappa tends to be soft and supple, saddle is stiffer, and nubuck is like suede;

c. Source—desirable is the natural hide of cattle that are 2-3 years old; older hides may be scarred and more rigid;

d. Color & finish—for example, aniline dyed (transparent dyes permeate the leather without significantly altering its appearance); surface coating (opaque sprays may hide imperfections of less expensive leather); saddlery (grain, texture and scarring are emphasized to imbue the leather with a rougher appearance and feel).

One supplier is Eagle Ottawa in Rochester Hills, Mich., which processes cattle hides for automobile manufacturers. Such suppliers process hides to meet the automakers' specifications.

Before choosing a leather for mass production, the OEM wants to inspect a representative sample of what the product will look and feel like. In the past, the task of loose grain sampling was done by the tedious sorting of hides to find the desired appearance.

Conventional approaches include scanning and making a plastic replication, perhaps in a half pipe format by 3-D printing. But such approaches do not address the appearance of loose grain on the leather. Even the replication process of creating embossing plates is not as consistent or precise in emulating natural markings.

Among the art considered in preparing this patent application are U.S. Pat. Nos. 4,294,650; 3,298,851; 5,750,160; DE 19851117; DE 10119494; CN 2028088220.

Such mold makers make a nickel mold of whatever the customer wants to replicate. Accuracy of such molds is due in part to a process of 'growing' the nickel plate one atom at a time. Their process includes making a silicone negative of the sample, then a nickel plate.

SUMMARY OF INVENTION

Improving on such practices, a leather supplier has designed a process to replicate specialized leather natural markings on actual leather using nickel plates.

One aspect of the innovative process is the deployment of a specially designed holder for metal plates to emboss leather by heat transference and pressure.

DETAILED DESCRIPTION OF THE INVENTION

FIGS. 1-7 illustrate smooth and embossed leather samples, tools made from those samples and leather replicated from those tools.

Figure 1:
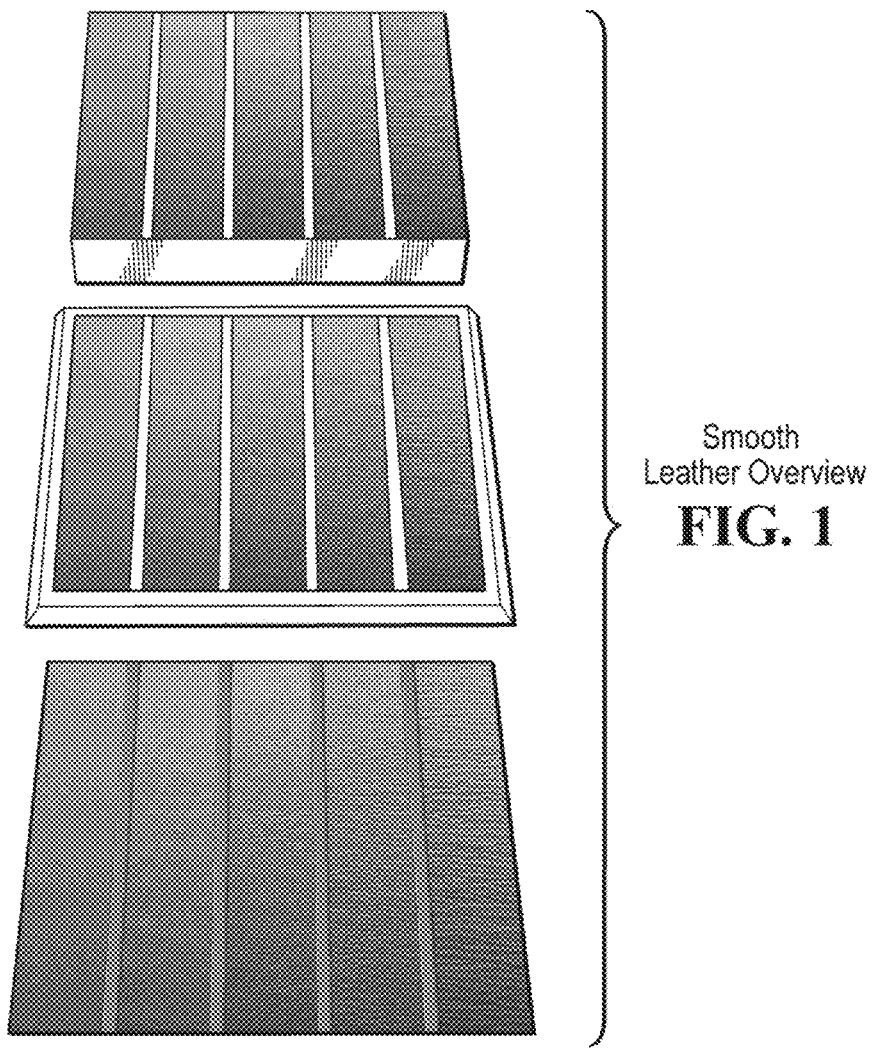
FIG. 1 is an overview of an original smooth leather sample, a mold/tool made from the original sample, and a finished, leather product-replicated.
Figure 2:
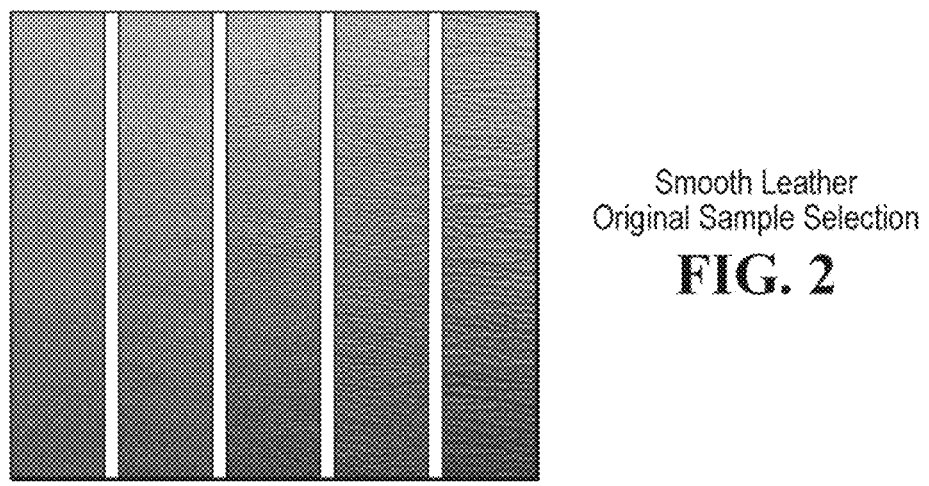
FIG. 2 depicts an original smooth leather sample for tool manufacturing.
Figure 6:
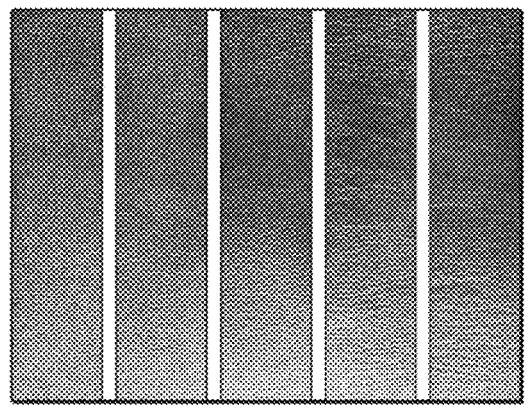
FIG. 6 depicts an embossed leather sample selection.
Figure 8:
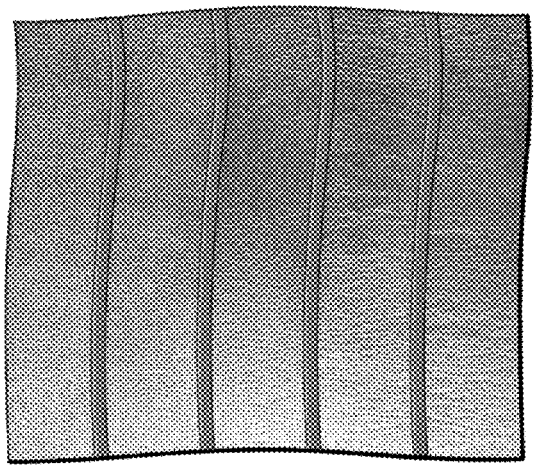
FIG. 8 depicts an embossed leather finished product-replicated leather.

In one variant of the disclosed practice, a mold maker may make a nickel copy of a piece of leather. The leather supplier then uses this plate to make faithful replicates of those swatches. These are some steps:

1. The leather supplier selects or designs samples of leather to be reproduced (FIGS. 2, 6). The samples could include any leather condition or appearance, (such as a natural marking, a good appearance, a bad appearance or otherwise. For some leather swatches (for example, with an embossed or smooth surface appearance), the leather supplier may need to replicate samples of a specific condition. Rather than using photographs, the supplier has realized that the product lends itself to applications in a flat state or a bent state. This can be compared to leather in various parts of for example a seat assembly process (inspecting leather, cutting leather, inspecting cut parts prior to and after sewing, and final assembly). By following the practices disclosed herein, the samples are unique in comparison with those represented by photos. This is partly because the processed leather sample (FIGS. 4, 8) can be compared directly to the original leather specimen (FIGS. 2, 6), and can be manipulated. Further, the operator can feel the leather, a factor that is desirable when working with leather. The supplier thus has created samples that represent what leather truly looks like, how it feels, and how it behaves.

2. The supplier then attaches film strips of the leather samples to a rendering board (e.g., a thick high-density foam board, FIGS. 2, 6) so that a mold maker can make a silicone negative from which a nickel mold can be made. In contrast to traditional methods, the process of adhering leather to the rendering board occurs in such a way as to avoid altering the leather.

Figure 3:
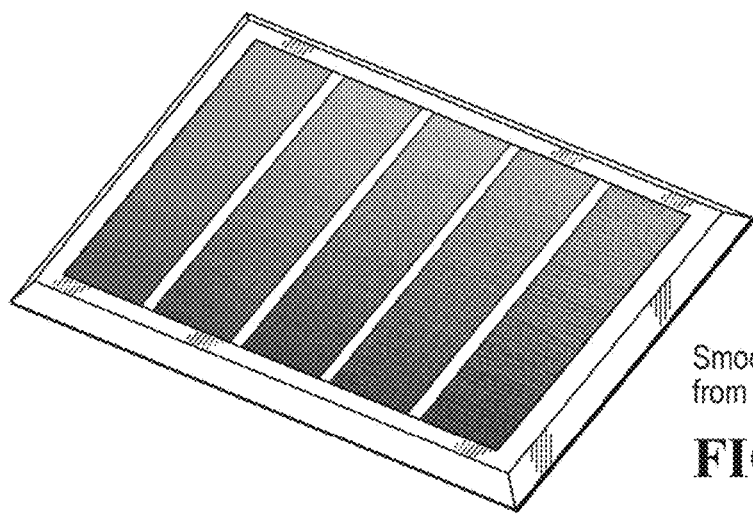
FIG. 3 depicts a smooth leather embossing tool; made from the sample of FIG. 2.
Figure 4:
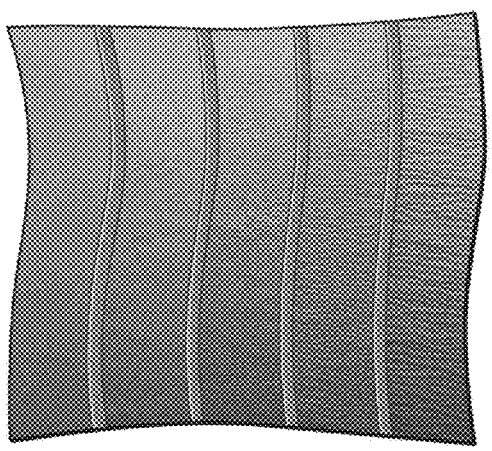
FIG. 4 depicts a smooth leather finished product-replicated leather.
Figure 5:
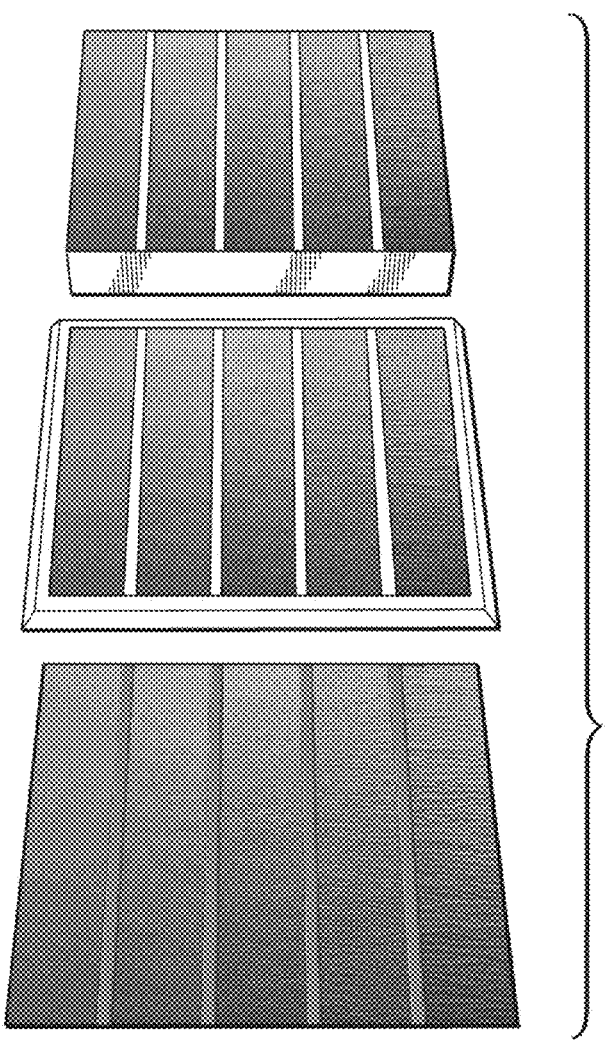
FIG. 5 depicts an embossed leather overview.
Figure 7:
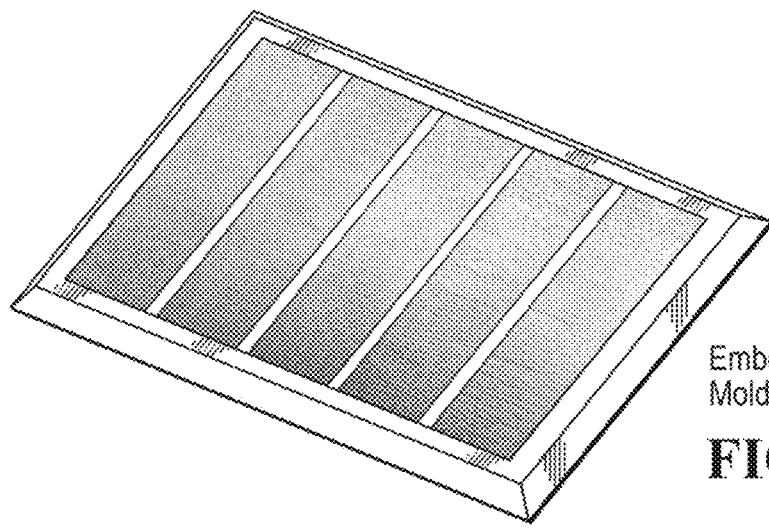
FIG. 7 depicts an embossed leather mold/tool made from the sample of FIG. 6.

3. One facet of the disclosed process is the use of a special plate holder to house/hold nickel plates (FIGS. 3, 7). The holder enables the nickel plates to emboss the leather on for instance a Mostardini embossing machine that uses heat and/or pressure to emboss leather.

4. In one variation, the supplier may select a conventionally finished split leather to emboss. Split leather is a conventionally finished product. After many trials, the supplier succeeded in optimizing replication from the nickel plate onto the leather. Preferably a final leather swatch is malleable and will not change upon manipulation. Such a leather can now be reliably embossed despite being in inventory for extended periods of time before embossing. Normally, the leather finisher wants to perform the embossing step in the middle of a potentially lengthy process, and not leave inventory the embossed leather in for too long. Replication from the nickel plate, which is 100% of the original master can now be achieved to a 97% level. While leather finishing and embossing are old in several respects, creation of such a high-fidelity product is unique.

5. In one set of experiments, the leather supplier designed samples in a film strip manner (FIGS. 2, 6) to replicate leather conditions not normally seen in a swatch format. These filmstrip samples of loose break/loose grain have applications for flat leather, half pipe leathers, and laminated leathers.

Thus, one aspect of this disclosure deals with a better way to replicate natural markings in leather. By following the practices described, problems of replicating a naturally marking with fidelity even after frequent mold are solved with a nickel plate instead of a silicone mold. As is known, a nickel plate normally does not degrade over time and can make samples in a flat state, for curved parts or for half-pipe parts. Preferably, a hard-tooled mold such nickel plates that are grown by successive atomic layers is preferable to a silicone mold for replication. Such a nickel plate is a nearly perfect emulation of the original sample.

In one process, a desired example of a surface characteristic (such as a scar) is found on a leather material sample (see, e.g. FIGS. 2, 6). The supplier offers the sample to a customer for approval. Upon approval, the supplier then makes a mold (FIGS. 3, 7) that is effectively a 3-D image of the sample to be reproduced, often using a specifically designed plate holder in specific embossing equipment. The holder engages the mold or molds (plates). Using heat and pressure, a leather workpiece is embossed, preferably to produce a specifically designed finish (FIGS. 4, 7) that in one case stays un-cross-linked for a long time to allow for storage and inventory management.

Such steps allow replication to an accuracy of around 97%, as appreciated upon examination of the replicated leather at the micron level under a high-power microscope. Degradation of the nickel plate is negligible, even after many samples are made.

One use for this technology is in replicating and controlling a natural hide condition that is unsuitable for secondary leather processes such as lamination of leather. Consider a loose break in a leather surface that is a characteristic of an animal where the angle of fibers or collagen in the hide changes directionally towards the belly of the hide. That creates a line appearance area which is unsuited for some secondary leather processes in which for example a piece of foam is laminated to the leather.

In some cases, the customer may not like the appearance of the leather with a loose break. In other cases, a leather cannot be laminated because it will wrinkle or 'grandfather'. Therefore, the supplier needs to make molds of these samples that can be evaluated in a flat state for visual inspection to determine acceptability—e.g., this sample is too poor, does not match the hide, or it has satisfied the customer's specifications. This allows leather manufacturers to avoid areas of the hide that cannot otherwise be deployed.

Alternatively, by using a variant of the disclosed process, the supplier can laminate a split leather and form a half-pipe. Furthermore, the supplier can if desired bond the leather. This is useful for some applications that need lamination and in portions of a seat that are concave.

To do this, two plates may be deployed. One is an embossed leather which often carries a lower price. Another is a smooth leather which typically carries a higher price. A loose break can look differently in either case.

Molded samples can be compared with leather in a flat state, such as when leather is cut into seats, or in assembled components such as the seats themselves. This is because the molded samples do not change their appearance under manipulation or bending. The condition of the leather is readily visible. Its condition can be assessed and judged with a higher accuracy in comparison with use of a photograph of a leather condition. As noted earlier, use of photos causes much confusion and wastage in the automotive leather supply chain.

Thus, one aspect of this disclosure deals with a process of using split leather and embossing plates to replicate loose grain in leather. This process allows for the mass reproduction of an appearance feature on leather with little or no variability in sampling. Thus, the discerning observer can select a leather for mass production with a high confidence level based on reliable inferences made about the product upon inspecting product samples.

To do this, unique tooling has been developed. The tooling recreates natural markings such as scars on hides. In one embodiment, a modular (flexible) die cut tool is used that is interchangeable and can cut for example a set of leather-foam pieces for many programs.

In use, the hard tool embosses natural markings on leather samples in a process that is repeatable, yet allows for variations in the appearance of the samples. This contrasts with laminated films and thus allows for increased flexibility in the substrates thus processed.

As a practical matter, the samples made with the disclosed tooling by the process described herein can be used as is, or bent and otherwise manipulated depending on the application. For example, a seat supplier can bend part of a seat, and a supplier of conforming leather can use the sample as-is in a flat state format or shape it into a half pipe format to enable a comparison of leather in its various states of manipulation.

To recap (FIGS. 1, 5), one way to practice the disclosed process for replicating a leather sampling, involves these steps:
1. Select leather samples that meet the desired criteria and create a sample board. (See, FIGS. 1, 6—original smooth/embossed leather samples for tool manufacturing);
   a. For example, 5 samples are selected and are embodied in film strips that depict leather looseness levels 1-5;
2. Send the leather sample board to a hard tool manufacturer to make a plate. (See, FIGS. 3, 7—smooth/embossed leather embossing tool); and
3. Use the plate to prepare molded leather samples. (See, FIGS. 4, 8—post-emboss molded leather smooth/embossed samples).

The molded leather samples may then be inspected by the customer to establish acceptable leather looseness limits and then used by the leather processor to inspect and adhere to those limits.

One embodiment of the hard tooling recreates natural markings such as scars on hides. The tooling optionally includes a modular (flexible) die cut tool that is interchangeable to cut a set of leather-foam pieces for many programs.

The hard tool embosses natural markings in a process that is more repeatable than those adopted conventionally and allows for variation in appearance of the material in samples thus made. Further, in contrast to most industry-adopted laminated films, the materials are conventionally finished. This allows the substrates to have more flexibility.

Figure 9:
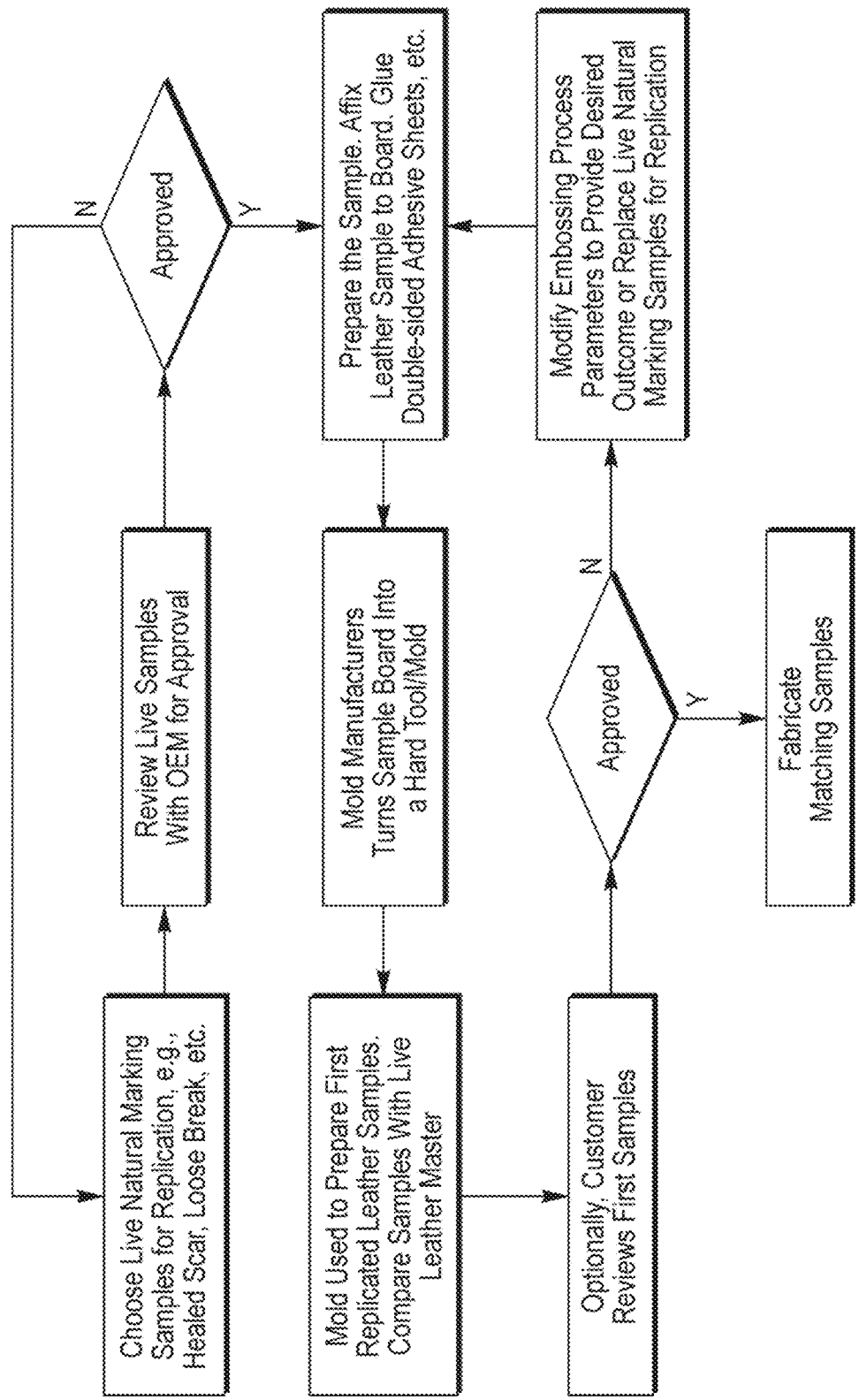
FIG. 9 is a flow chart that interrelates several of the process steps in one way to practice the disclosed method.

FIG. 9 illustrates one way to practice the process steps described:
A. Choose samples for replication;
B. Review samples with the customer for approval;
C. Give the approved samples to a mold manufacturer to make replication tools;
D. Ship the molds to the sample manufacturer;
E. Produce molded samples;
F. Give the molded samples to the customer for inspection and approval;
G. Replicate the approved samples by fabricating molded loose grain samples per the customer's specification. Such samples can then be reviewed with the customer to establish acceptable leather looseness limits.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of components. Therefore, specific structural and functional details disclosed herein are not to be interpreted as limiting, but merely as a representative basis for teaching one skilled in the art to variously employ the present invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

We claim:

1. A method for replicating leather comprising the steps of:
   (A) choosing original samples of leather for replication, the original samples including a characteristic to be replicated and preparing strips of the original samples, the strips containing side-by-side arrangements of specimens having characteristics desired for replication;
   (B) optionally reviewing the original samples with a customer for approval to confirm approved samples;

(C) making a replication tool from the original samples;
(D) optionally delivering the replication tool to a sample manufacturer;
(E) producing replicated molded samples with the replication tool that emulate the original samples, thereby enabling the replicated molded samples to be compared with the original samples, the replicated molded samples not changing their appearance upon manipulation;
(F) optionally presenting the replicated molded samples to the customer for inspection and approval to confirm finished replicated molded samples; and
(G) optionally reproducing the finished replicated molded samples.

2. The method of claim 1 wherein step (C) includes the steps of:
(C1) applying a material to a surface of the original samples so that a 3-D image of surface characteristics of the original samples is formed;
(C2) depositing a fluid metallic layer on the 3-D image so that surface characteristics of the original samples appear laterally inverted in a metallic form, the metallic form after cooling comprising a solidified mold.

3. The method of claim 2 wherein the material of step (C1) includes silicone.

4. The method of claim 2 wherein step (C2) further includes the step of making a holder that includes metallic strips of the metallic form.

5. The method of claim 1 wherein the characteristic to be replicated includes a feature selected from the group consisting of a scar, an insect bite, a natural marking, a good appearance, a bad appearance, another surface feature and a tear.

6. A method for replicating leather comprising the steps of:
(H) choosing original samples for replication, the original samples including a characteristic to be replicated and preparing strips of the original samples, the strips containing side-by-side arrangements of specimens having characteristics desired for replication;
(I) making a replication tool from the samples;
(J) producing replicated molded samples with the replication tool that emulate the original samples, thereby enabling the replicated molded samples to be compared with the original samples, the replicated molded samples not changing their appearance under manipulation.

7. The method of claim 6, further including this step between steps (H) and (I):
reviewing the original samples with a customer for approval to confirm approved samples.

8. The method of claim 6, further including this step between steps (I) and (J):
delivering the replication tool to a sample manufacturer.

* * * * *